(12) United States Patent
Newbolt

(10) Patent No.: US 7,776,276 B1
(45) Date of Patent: Aug. 17, 2010

(54) AIR FILTERING SYSTEM FOR A VEHICLE PASSENGER COMPARTMENT

(76) Inventor: Veltilena Newbolt, 17101 Mountain Crest Ct., Riverside, CA (US) 92503

(*) Notice: Subject to any disclaimer, the term of this patent is extended or adjusted under 35 U.S.C. 154(b) by 0 days.

(21) Appl. No.: 12/266,074

(22) Filed: Nov. 6, 2008

Related U.S. Application Data

(60) Provisional application No. 60/985,689, filed on Nov. 6, 2007.

(51) Int. Cl.
*A61L 9/00* (2006.01)

(52) U.S. Cl. .......................... 422/120; 422/5; 422/123; 422/124

(58) Field of Classification Search ...................... 422/5, 422/120, 123, 124
See application file for complete search history.

(56) References Cited

U.S. PATENT DOCUMENTS

| | | | | |
|---|---|---|---|---|
| 2,383,423 A | * | 8/1945 | Steins | 454/99 |
| 4,541,847 A | * | 9/1985 | Oie et al. | 96/58 |
| 4,658,707 A | * | 4/1987 | Hawkins et al. | 454/75 |
| 5,297,988 A | * | 3/1994 | Nishino et al. | 454/75 |

* cited by examiner

*Primary Examiner*—Sean E Conley
(74) *Attorney, Agent, or Firm*—Kenneth L Tolar

(57) ABSTRACT

An air filtering system for a vehicle includes a housing having a fan, a HEPA filter, a carbon-impregnated military cloth and a scent dispersing mechanism received therein. Air intake modules are positioned at desired locations within the vehicle passenger compartment, each of which is in communication with the housing interior. To remove smoke or other pollutants, a passenger activates the fan to deliver ambient air to the housing interior whereby the HEPA filter removes particles while the charcoal cloth removes entrained odors. The housing also includes a fragrance dispenser for dispersing a scented material, if desired.

5 Claims, 2 Drawing Sheets

AIR FILTERING SYSTEM FOR A VEHICLE PASSENGER COMPARTMENT

CROSS REFERENCE TO RELATED APPLICATIONS

This application is entitled to the benefit of provisional application No. 60/985,689 filed on Nov. 6, 2007, the specification of which is incorporated herein by reference.

BACKGROUND OF THE INVENTION

The present invention relates to a device for removing smoke and other noxious fumes from a vehicle passenger compartment.

DESCRIPTION OF THE PRIOR ART

When vehicle passengers smoke cigarettes or cigars, the passenger compartment is bombarded with second-hand smoke that infiltrates the upholstery and aggravates other passengers. Though some of the smoke may be removed by lowering a window, such an option is impractical during inclement weather. In addition, the vehicle's air conditioning system is capable of removing only a small portion of the accumulated smoke. Accordingly, there is currently a need for a device that quickly removes cigarette smoke and other pollutants from a vehicle passenger compartment. The present invention addresses this need by providing a uniquely-designed air filtering system for a vehicle passenger compartment.

SUMMARY OF THE INVENTION

An air filtering system for a vehicle includes a housing having a fan, a HEPA filter, a carbon-impregnated military cloth and a scent dispersing-mechanism received therein. Air intake modules are positioned at strategic locations within the vehicle passenger compartment, each of which is in communication with the housing interior. To remove smoke or other pollutants, a passenger activates the fan to deliver ambient air to the housing interior where the HEPA filter removes particles while the charcoal cloth removes entrained odors. The housing also includes a fragrance dispenser for dispersing a scented material, if desired.

It is therefore an object of the present invention to provide an air filtering system that removes cigarette smoke and other pollutants from a vehicle passenger compartment.

It is another object of the present invention to provide an air filtering system that dispenses a fragrant material to a vehicle passenger compartment.

Other objects, features, and advantages of the present invention will become readily apparent from the following detailed description of the preferred embodiment when considered with the attached drawings and the appended claims.

DESCRIPTION OF THE PREFERRED EMBODIMENT

Figure 1:
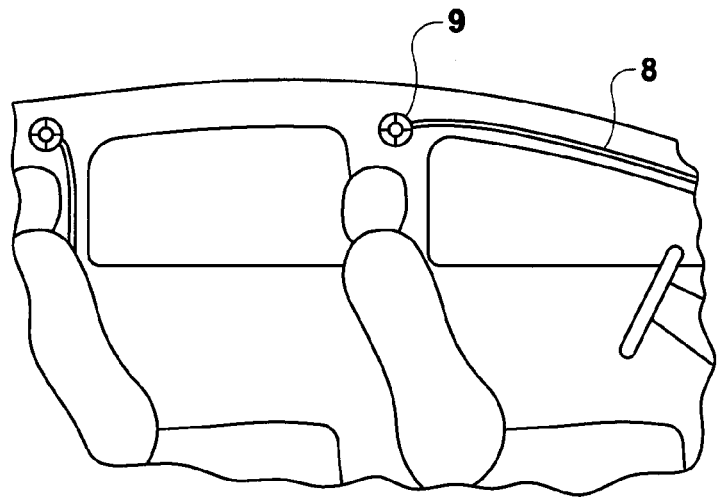
FIG. 1 is a side view of a vehicle passenger compartment depicting the air intake modules mounted therein.
Figure 2:
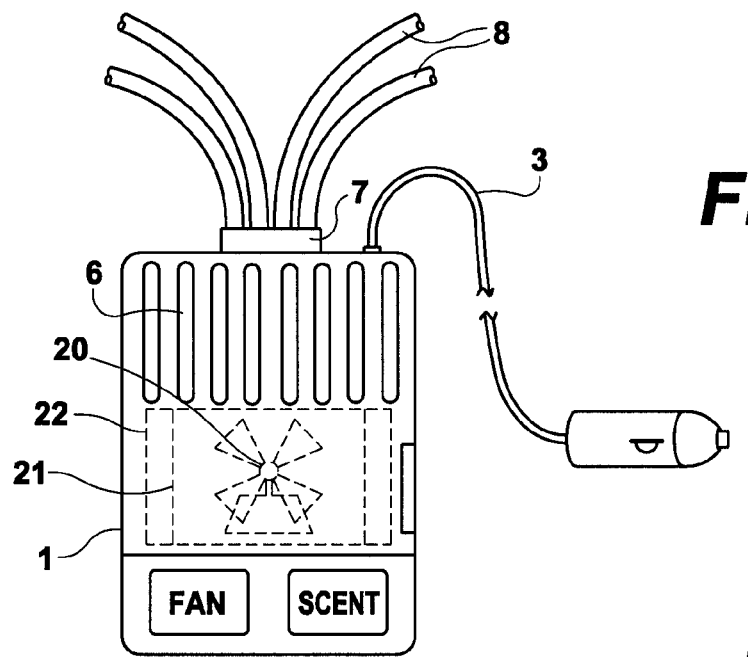
FIG. 2 is a front view of the housing.
Figure 3:
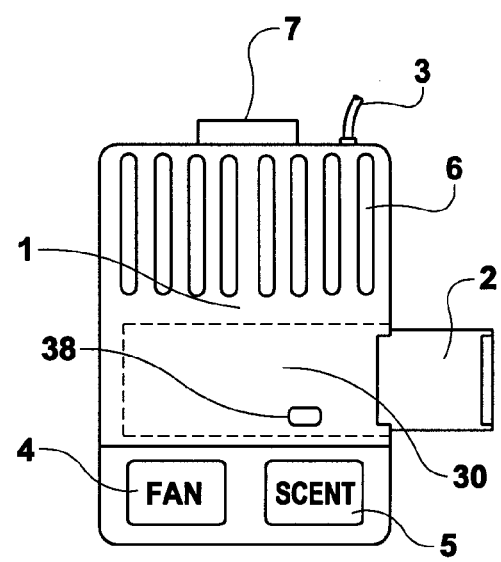
FIG. 3 depicts the fragrance cartridge being removed from the housing.
Figure 4:
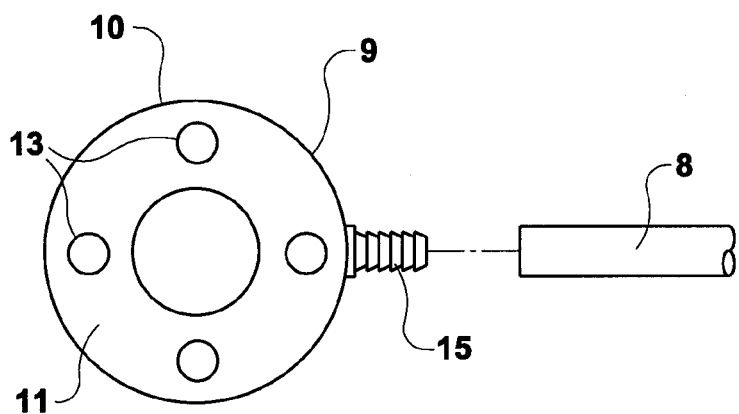
FIG. 4 is a front view of an exemplary air intake module.
Figure 5:
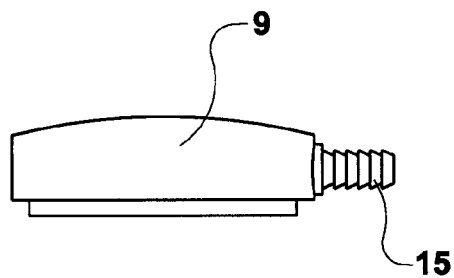
FIG. 5 is a side view of an exemplary air intake module.
Figure 6:
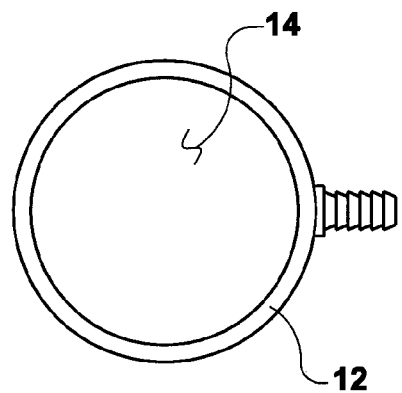
FIG. 6 is a rear view of an exemplary air intake module.

The present invention relates to a smoke vacuum for a vehicle. The device comprises a housing 1 having a front surface, an interior chamber and an upper end. Received within the interior is a fan 20, a HEPA filter 21, a carbon-impregnated military cloth 22 and a scent-dispersing mechanism. The scent-dispersing mechanism includes a cartridge 2 having a fragrant material received therein; the cartridge is removably received within a compartment 30 allowing it to be easily removed and replaced as necessary. The fan and scent-dispersing mechanism are powered with a cord 3 that is coupled with the vehicle's cigarette lighter/adapter. A first button 4 on the front surface of the housing activates the fan while a second button 5 activates a solenoid valve 38 that is in fluid communication with the cartridge; accordingly, when the button 5 is depressed, the scented material gravity feeds into filtered, deodorized outlet air prior to exiting air vents 6.

On the upper end of the housing is an opening 7 for receiving a plurality of air inlet tubes 8. Attachable to a distal end of each tube is an air intake module 9 including a casing 10 having a front surface 11 and a rear surface 12. A plurality of air inlet openings 13 are peripherally positioned on the front surface, while an adhesive 14 is positioned on the rear surface for securing the casing to a desired surface within the passenger compartment. A barbed fitting 15 is positioned on an outer edge of the casing to which the tube 8 is secured.

The intake modules are adhesively attached to the interior of the passenger compartment at locations where smoke concentration is likely to be high. A tube from the housing is connected to the barbed fitting on each intake module. To remove smoke or other noxious gases, a passenger depresses the first button to activate the fan whereby ambient air is delivered to the housing interior; the HEPA filter removes particles while the charcoal-impregnated cloth removes entrained odors. If the passenger wishes to dispense a scented material, he or she depresses the second button to activate the scent dispersing mechanism. The removable cartridge releases a few drops of the fragrant material, which the fan disperses into the passenger compartment.

The above-described device is not limited to the exact details of construction and enumeration of parts provided herein. Furthermore, the size, shape and materials of construction of the various components can be varied.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

The invention claimed is:

1. An air freshening system in combination with a vehicle passenger compartment comprising:
    a housing having a front surface and an interior chamber;
    a freshener means for removing particulate matter and odors from ambient air within the passenger compartment, said freshener means including a fan, a filter and a carbon-impregnated cloth received within the interior chamber of said housing;
    a plurality of air-intake modules positioned within said vehicle passenger compartment, each of said modules including a casing having an outer edge, a front surface and a rear surface, said front surface having a plurality of air inlet openings peripherally positioned thereon, a barbed fitting positioned on the outer edge of said casing, said fitting in communication with said air inlet openings;

a tube secured to said barbed fitting, said tube in communication with said freshener means and extending into the interior chamber of said housing.

2. The air freshening system according to claim 1 further comprising an adhesive positioned on the rear surface of said casing for securing the casing to a desired surface within said passenger compartment.

3. The air freshening system according to claim 1 further comprising a scent-dispersing means for dispersing a scented substance to said passenger compartment.

4. The air freshening system according to claim 1 wherein said fan is activated by a first button on a surface of the housing.

5. The air freshening system according to claim 3 wherein said scent-dispersing means comprises:

a cartridge removably received within said housing, said cartridge having a scented material received therein;

a solenoid valve in fluid communication with said cartridge;

a second button on said housing for opening said solenoid valve to dispense the scented material to air flowing to said passenger compartment.

* * * * *